United States Patent
Gaffar et al.

[11] Patent Number: 6,136,298
[45] Date of Patent: Oct. 24, 2000

[54] PROCESS FOR INHIBITING S. MUTANS AND CARIES

[75] Inventors: Abdul Gaffar, Princeton; Nuran Nabi, Cranbury; John J. Afflitto, Brookside, all of N.J.

[73] Assignee: Colgate-Palmolive Company, New York, N.Y.

[21] Appl. No.: 09/234,246

[22] Filed: Jan. 20, 1999

Related U.S. Application Data

[63] Continuation-in-part of application No. 08/968,671, Nov. 12, 1997, abandoned.

[51] Int. Cl.[7] ............................... A61K 7/16; A61K 7/18
[52] U.S. Cl. ................................... 424/49; 424/52
[58] Field of Search ............................. 424/49–58

[56] References Cited

U.S. PATENT DOCUMENTS

| | | |
|---|---|---|
| 3,932,604 | 1/1976 | Barth . |
| 4,022,880 | 5/1977 | Vinson et al. . |
| 4,111,844 | 9/1978 | Polony et al. . |
| 4,894,220 | 1/1990 | Nabi et al. . |
| 4,980,153 | 12/1990 | Jackson et al. . |
| 5,032,385 | 7/1991 | Reed et al. . |
| 5,032,386 | 7/1991 | Gaffar et al. . |
| 5,043,154 | 8/1991 | Gaffar et al. . |
| 5,089,255 | 2/1992 | Gaffar et al. . |
| 5,178,851 | 1/1993 | Gaffar et al. . |
| 5,192,530 | 3/1993 | Gaffar et al. . |
| 5,344,641 | 9/1994 | Gaffar et al. . |
| 5,424,059 | 6/1995 | Prencipe et al. . |
| 5,531,982 | 7/1996 | Gaffar et al. . |
| 5,538,715 | 7/1996 | Gaffar et al. . |

FOREIGN PATENT DOCUMENTS

| | | |
|---|---|---|
| 161898 | 11/1990 | European Pat. Off. . |
| 3532860 | 3/1987 | Germany . |

OTHER PUBLICATIONS

Svanberg et al Caries Res. 25(6): 449–453 (xylitol in dentifrices significantly reduces S. mutans), (1991).

Cutress et al J. Dent. Child. 59(4): 313–318 (caries preventive effects of high fluoride & and xylitol dentifrices), (1992).

Isokangas et al. "Xyitol Chewing Gum in Caries Prevention: A Field Study in Children", JADA, vol. 117, Aug. 1888, pp. 315–320.

Loesche et al, "The Effect of Chewing Xytitol Gum on the Plaque and Saliva Levels of Streptococcus Mutans", JADA, vol. 108, Apr. 1984, pp. 587–592.

Assev et al, "Further Studies on the Growth Inhibition of Streptococcus Mutans OMZ 176 by Xylitol", Acta Path. Microbiol. Immunol. Scand. Sect. B, 94:97–102, 1986.

Bär, Albert "Caries Prevention with Xylitol"; World Review of Nutrition and Dietetics, vol. 55:183, 1988.

*Primary Examiner*—Shep K. Rose
*Attorney, Agent, or Firm*—Henry S. Goldfine; Paul Shapiro

[57] ABSTRACT

A process which inhibits bacteria and caries comprising the application of an oral composition containing a substantially water insoluble noncationic antimicrobial agent, such as triclosan, xylitol, and sodium lauryl sulfate as the surfactant and dispersant for the water insoluble noncationic antimicrobial agent.

16 Claims, No Drawings

PROCESS FOR INHIBITING S. MUTANS AND CARIES

This application is a continuation-in-part of application Ser. No. 08/968,671 filed Nov. 12, 1997, now abandoned.

BACKGROUND OF THE INVENTION

I. Field of the Invention

This invention relates to a method for reducing the incidence of oral caries, more particularly, it relates to the application to oral surfaces of a sodium lauryl sulfate containing oral composition comprising a combination of antibacterial agents effective against streptococcus mutans and consequently reduce the incidence of caries.

II. Prior Art

It is known that dental caries are caused by the production of acid by certain specific bacteria. The particular bacteria generally recognized as the major etiological factor in dental caries is *Streptococcus mutans* (hereinafter *S. mutans*). *S. mutans* produce extacellular glucosyl and fructosal transferases enzymes from sugars which catalyze the formation of sticky, adhesive glucans and fructans from sucrose, which in turn promote the adhesion of bacteria to the oral surfaces. Further, *S. mutans* mutiple in the human environment and are a very high acid producer relative to other oral microorganisms.

Repeated cycles of such acid attack to tooth enamel initially results in microscopic demineralization or decalcification of the hydroxyapatite structure of the tooth enamel and the formation of an incipient carious lesion therein. While saliva provides a continuing source of calcium and phosphate to the tooth enamel which tends to remineralize the hydroxyapatite structure of the enamel, inhibiting and reversing the demineralizing carious process; once the acid attack has caused the demineralization to proceeded beyond an as yet not clearly defined state, the development of a full-fledged carious lesion and a clinically evident cavity occurs.

Dental plaque is a soft material formed of a complex mass of the bacteria that adherses to the very thin pellicle layer, formed primarily of salivary proteins, which surround each tooth. A 5-day-old plaque, if not disrupted as by brushing, can reach a thickness of about 60 m$\mu$. A cariogenic plaque containing a high proportion of *S. mutans*, can often contain $2 \times 10^8$ bacteria per mg wet weight and can rapidly ferment sucrose, glucose, or fructose to generate enough acid to lower the pH of the plaque to 5.5 or lower; whereupon demineralization of surface enamel occurs.

In the past, the main approach to reduction of caries has been the use of fluorides. The efficacy of fluorides in reducing caries is believed to be their direct inhibitory effect on enamel demineralization and promotion of the remineralization process. Indeed in U.S. Pat. No. 5,089,255, to Gaffar et al, remineralization is taught to be promoted by fluoride and xylitol. However, generally the maximum amount of fluoride ion approved by the U.S. Food and Drug Administration (FDA) for use in over-the-counter dentifrice formulations is limited to 1150 ppm.

An alternate or supplemental approach to fluorides is use of agents which effectively inhibit acid production by the bacteria within the plaque. This can be accomplished either by killing or removing the plaque and/or its constituent acidogenic bacteria or by inhibiting the bacterial metabolic processes, in particular the fermentation of carbohydrates and glucose to produce acid. Bactericidal compounds can, in theory, accomplish this, if they are suitably formulated and delivered, and have sufficient substantivity and efficacy.

*S. mutans* and dental plaque in general require the fermentation of substrates, not only as an energy source, but also for the production of structural and adhesion macromolecules like extracellular polysaccharides (glucans and fructans), lipoteichoic acid (LTA) and lectins. Xylitol, appears to cause a disturbance in the metabolism of fermentable carbohydrate by *S. mutans* and thereby decreases plaque formation and reduces plaque adhesion to the pellicle. Further, it is theorized that a toxic metabolite (xylitol-5-phosphate) is formed within the *S. mutans* cells, which may interfere with the glycolysis energy production and may also involve an energy-consuming futile cycle. These effects result in reduced caries, as has been documented by studies in humans employing high frequency use of xylitol in place of dietary sucrose, as well as, studies in candies and gums (e.g. Bär, Albert "Caries Prevention with Xylitol"; World Review of Nutrition and Dietetics, vol. 55:183, 1988).

Surface active agents or surfactants are required in dentifrice formulations to aid in the thorough dispersion of the dentifrice throughout the oral cavity when applied thereto, as well as, improve the dentifrice's cosmetic acceptability and the foaming properties. Sodium lauryl sulfate (hereinafter SLS) has supplanted virtually all other surfactants as the foaming agent in dentifrices, whereby roughly 4 million pounds of SLS is used in oral products in the U.S. annually (Pader, *Oral Hygiene Products and Practice*, Marcel Dekker, Inc., N.Y., 1988). Previously, it had been concluded that the use of xylitol in toothpaste containing SLS would not have any antibacterial or caries reducing effect (Assev and Rolla, "SLS Containing Toothpaste Is Not A Suitable Vehicle For Xylitol", J. Dental Res., 75:316 (IADR Abstracts) 1996). This conclusion has been theorized to be due to SLS inhibiting the uptake of xylitol and inhibiting the formation of xylitol-5-phosphate (Jannesson et al., "Effect Of Xylitol In An Enzyme-Containing Dentifrice Without Sodium Lauryl Sulfate On Mutans Streptococci In Vivo", Acta Odontol Scand 55:212 (1997)).

U.S. Pat. No. 5,531,982 discloses an oral composition which inhibits plaque and reduces gingivitis and caries comprising a substantially water insoluble noncationic antimicrobial agent, such as triclosan, an acid reducing agent, such as xylitol and a water-insoluble siliceous polishing agent, further discloses the use therein of organic surface active agents, preferably anionic, nonionic or ampholytic in nature, examples of which include sodium lauryl sulfate. U.S. Pat. No. 5,531,982 by requiring a water-insoluble siliceous polishing agent is unduly limiting with respect to forumulation.

In companion co-pending U.S. patent application Ser. No. 08/160,337, filed Dec. 1, 1993, now U.S. Pat. No. 5,538,715, belonging to the same party-in-interest, an antibacterial antiplaque dentifrice was disclosed containing as an antibacterial agent, a substantially water-insoluble noncationic antibacterial agent such as triclosan, a antibacterial-enhancing agent and a solubilizing agent. U.S. Pat. No. 5,538,715 also disclosed the use therein of xylitol as an alternative sweetening agent. Such use of xylitol as a sweetener or a humectant in oral compositions which may or may not contain a noncationic antibacterial agent, such as triclosan, is known in the art.

There is a clear need in the art to for SLS containing oral compositions having anticaries efficacy as an alternative or supplement to the use of fluoride, that provide significant *S. Mutans* reduction and consequently reduce the incidence of caries formation and that are not unduly limited.

SUMMARY OF THE INVENTION

This invention relates to a method for reducing the incidence of caries by the application to the oral surfaces of an oral composition comprising, an effective antibacterial amount of a substantially water insoluble noncationic antibacterial agent, at least about 0.1% by weight of xylitol, and as a surface active agent and/or dispersant for said antibacterial agent at least 0.5% sodium lauryl sulfate; wherein such application surprisingly reduces the *S. Mutans* bacteria in the presence of the sodium lauryl sulfate.

DESCRIPTION OF THE PREFERRED EMBODIMENTS

Typical examples of water insoluble noncationic antibacterial agents which are particularly desirable from considerations of effectiveness, safety and formulation are:

Halogenated Diphenyl Ethers

2',4,4'-trichloro-2-hydroxy-diphenyl ether (triclosan)
2,2'-dihydroxy-5,5'-dibromo-diphenyl ether

Benzoic Esters

Methyl-p-Hydroxybenzoic Ester
Ethyl-p-Hydroxybenzoic Ester
Propyl-p-Hydroxybenzoic Ester
Butyl-p-Hydroxybenzoic Ester

Sesquiterpene Alcohols

Farnesol
Nerolidol
Bisabolol
Santalol

Halogenated Carbanilides 3,4,4'-trichlorocarbanilide
3-trifluoromethyl-4,4'-dichlorocarbanilide
3,3,4'-trichlorocarbanilide Phenolic Compounds (including phenol and its homologs, mono- and poly-alkyl and aromatic halo (e.g. F, Cl, Br, I)-phenols, resorcinol and catechol and their derivatives and bisphenolic compounds). Such compounds include inter alia:

Phenol and its Homologs

Phenol
2 Methyl-Phenol
3 Methyl-Phenol
4 Methyl-Phenol
4 Ethyl-Phenol
2,4-Dimethyl-Phenol
2,5-Dimethyl-Phenol
3,4-Dimethyl-Phenol
2,6-Dimethyl-Phenol
4-n Propyl-Phenol
4-n-Butyl-Phenol
4-n-Amyl-Phenol
4-tert-Amyl-Phenol
4-n-Hexyl-Phenol
4-n-Heptyl-Phenol 2-Methoxy-4-(2-Propenyl)-Phenol (Eugenol)
2-Isopropyl-5-Methyl-Phenol (Thymol)

Mono- and Poly-Alkyl and Aralkyl Halophenols

Methyl-p-Chlorophenol
Ethyl-p-Chlorphenol
n-Propyl-p-Chlorophenol
n-Butyl-p-Chlorophenol
n-Amyl-p-Chlorophenol
sec-Amyl-p-Chlorophenol
n-Hexyl-p-Chlorophenol
Cyclohexyl-p-Chlorophenol
n-Heptyl-p-Chlorophenol
n-Octyl-p-Chlorophenol
O-Chlorophenol
Methyl-o-Chlorophenol
Ethyl-o-Chlorophenol
n-Propyl-o-Chlorophenol
n-Butyl-o-Chlorophenol
n-Amyl-o-Chlorophenol
tert-Amyl-o-Chlorophenol
n-Hexyl-o-Chlorophenol
n-Heptyl-o-Chlorophenol
p-Chlorophenol
o-Benzyl-p-Chlorophenol
o-Benzyl-m-methyl-p-Chlorophenol
o-Benzyl-m,m-dimethyl-p-Chlorophenol
o-Phenylethyl-p-Chlorophenol
o-Phenylethyl-m-methyl-p-Chlorophenol
3-Methyl-p-Chlorophenol
3,5-Dimethyl-p-Chlorophenol
6-Ethyl-3-methyl-p-Chlorophenol
6-n-Propyl-3-methyl-p-Chlorophenol
6-iso-propyl-3-methyl-p-Chlorophenol
2-Ethyl-3,5-dimethyl-p-Chlorophenol
6-sec Butyl-3-methyl-p-Chlorophenol
2-iso-Propyl-3,5-dimethyl-p-Chlorophenol
6-Diethylmethyl-3-methyl-p-Chlorophenol
6-iso-Propyl-2-ethyl-3-methyl-p-Chlorophenol
2-sec Amyl-3,5-dimethyl-p-Chlorophenol
2-Diethylmethyl-3,5-dimethyl-p-Chlorophenol
6-sec Octyl-3-methyl-p-Chlorophenol
p-Bromophenol
Methyl-p-Bromophenol
Ethyl-p-Bromophenol
n-Propyl-p-Bromophenol
n-Butyl-p-Bromophenol
n-Amyl-p-Bromophenol
sec-Amyl-p-Bromophenol
n-Hexyl-p-Bromophenol
cyclohexyl-p-Bromophenol
o-Bromophenol
tert-Amyl-o-Bromophenol
n-Hexyl-o-Bromophenol
n-Propyl-m,m-Dimethyl-o-Bromophenol
2-Phenyl Phenol 4-Chloro-2-methyl phenol
4-chloro-3-methyl phenol
4-chloro-3,5-dimethyl phenol
2,4-dichloro-3,5-dimethyl phenol
3,4,5,6-tetrabromo-2-methylphenol
5-methyl-2-pentylphenol
4-isopropyl-3-methylphenol
5-chloro-2-hydroxydiphenyl methane Resorcinol and its Derivatives Resorcinol
Methyl-Resorcinol
Ethyl-Resorcinol
n-Propyl-Resorcinol
n-Butyl-Resorcinol
n-Amyl-Resorcinol
n-Hexyl-Resorcinol
n-Heptyl-Resorcinol
n-Octyl-Resorcinol
n-Nonyl-Resorcinol
Phenyl-Resorcinol
Benzyl-Resorcinol
Phenylethyl-Resorcinol
Phenylpropyl-Resorcinol
p-Chlorobenzyl-Resorcinol
5-Chloro-2,4-Dihydroxydiphenyl Methane
4'-Chloro-2,4-Dihydroxydiphenyl Methane
5-Bromo-2,4-Dihydroxydiphenyl Methane
4'-Bromo-2,4-Dihydroxydiphenyl Methane Bisphenolic Compounds Bisphenol A
2,2'-methylene bis (4-chlorophenol)
2,2'-methylene bis (3,4,6-trichlorophenol) (hexachlorophene)
2,2'-methylene bis (4-chloro-6-bromophenol)
bis (2-hydroxy-3,5-dichlorophenyl) sulfide
bis (2-hydroxy-5-chlorobenzyl) sulfide The noncationic antibacterial agent is present in the dentifrice in an effective antiplaque amount, typically about 0.01–5% by weight, preferably about 0.03–1.0% by weight and most preferably about 0.3–0.5% by weight. The antibacterial agent is substantially water-insoluble, meaning that its solubility is less than about 1% by weight in water at 25° C. and may be even less than about 0.1% by weight.

The preferred halogenated diphenyl ether and most preferred noncationic antibacterial agent is triclosan. Preferred other noncationic antibacterial agents are hexyl resorcinol and 2,2'methylene bis (4-chloro-6-bromophenol).

Triclosan is disclosed in U.S. Pat. No. 4,022,880 as an antibacterial agent in combination with an anticalculus agent which provides zinc ions and in German Patent Disclosure 3532860 in combination with a copper compound. In European Patent Disclosure 0278744 it is disclosed in combination with a tooth desensitizing agent containing a source of potassium ions. It is also disclosed as an antiplaque agent in an oral composition formulated to contain a lamellar liquid crystal surfactant phase having a lamellar spacing of less than 6.0 nm and which may optionally contain a zinc salt in published European Patent Application 0161898 of Lane et al and in a dentifrice containing zinc citrate trihydrate in published European Patent Application 0161899 to Saxton et al.

Xylitol, when present in amounts ranging from about 0.1% by weight to about 40% by weight, surprisingly enhances the antibacterial and anticaries properties of the oral compositions of the present invention, considering the presence of sodium lauryl sulfate surfactants. In amounts ranging upward from 0.1% by weight to about 5% or more by weight, xylitol provides desirable sweetening to the oral composition, when present as the only sweetener, or desirably when mixed with another sweetener. The xylitol also provides desirable humectant character to the oral composition and can be the sole humectant particularly when present in amounts of about 20–40%, although it is desirably mixed with another humectant. Preferably, to provide the desired antibacterial activity and resultant anticaries benefits in the oral compositions of the present invention, xylitol is present in amount of about 1–30% by weight, more preferably about 3–25%, and most preferably about 5–15%.

In this invention, the oral composition dentifrice may be substantially a dental cream, toothpaste or gel dentifrice, containing a polishing agent which could be transparent, translucent or opacified, or a mouthwash or dental gel, which does not contain a polishing agent. Useful polishing agents include silicas, hydrated alumina, calcined alumina, sodium metaphosphate, sodium bicarbonate, calcium carbonate, calcium pyrophosphate, dicalcium phosphate and dicalcium phosphate dihydrate, wherein preferred are siliceous polishing materials which include crystalline silica having particle sized of up to about 5 microns, a mean particle size of up to about 1.1 microns, and a surface area of up to about 50,000 $cm^2$/gm, silica gel or colloidal silica and complex amorphorous alkali metal aluminosilicate; such preferred silicas include those sold under the tradenames of Tixosil 103 from Rhone-Poulenc, Cranbury, N.J. and Zeodent 115 from J. M. Huber Chemicals Division, Havre de Grace, Md.

When visually clear or opacified gels are employed, a polishing agent of colloidal silica, such as those sold under the trademark SYLOID from W. R. Grace/Davison Chemical in Baltimore, Md., as Syloid 72 and Syloid 74 or alkali metal aluminosilicate complexes (that is, silica containing alumina combined in its matrix) are particularly useful, since they are consistent with gel-like texture and have refractive indices close to the refractive indices of gelling agent-liquid (including water and/or humectant) systems commonly used in dentifrice.

The polishing material is generally present in the oral composition dentifrices such as toothpaste cream paste or gel compositions in weight concentrations of about 5% to about 30%.

In embodiments of oral compositions, an orally acceptable vehicle including a water-phase with humectant is present. As stated, xylitol can be the sole humectant, although it is preferably mixed with another humectant, preferably glycerine and/or sorbitol. In a dentifrice, water is present typically in amount of about 3% to 40% by weight, more typically about 10%–35%, and humectant typically in amount of about 6.5%–80%, such as about 10%–80%, preferably about 20%–75% by weight of the oral composition, more typically about 25–60%. Reference hereto to sorbitol refers to the material typically as available commercially in 70% aqueous solutions. In clear gels where the refractive index is an important consideration, about 3–30% of water, 0% to about 70% of glycerine and about 20–25% of sorbitol are preferably employed.

The oral composition dentifrices and dental gels typically contain a natural or synthetic thickener or gelling agent in proportions of about 0.1 to about 10% by weight, preferably about 0.5 to about 5% in a dentifrice and about 4–10% in a dental gel. A suitable thickener is synthetic hectorite, a synthetic colloidal magnesium alkali metal silicate complex clay available for example as Laponite. Laponite D analysis shows, approximately by weight, 58.00% $SiO_2$, 25.40% MgO, 3.05% $Na_2O$, 0.98% $Li_2O$, and some water and trace metal. Its true specific gravity is 2.53 and it has an apparent bulk density (g./ml. at 8% moisture) of 1.0.

Other suitable gelling agents or thickeners include organic thickeners, such as natural and synthetic gums and colloids. Examples of such organic thickeners include carrageenan (Irish moss), xanthan gum and sodium carboxymethyl cellulose, starch, polyvinylpyrrolidone, hydroxyethylpropyl cellulose, hydroxybutyl methyl cellulose, hydroxypropylmethyl cellulose, and hydroxyethyl cellulose. Inorganic thickeners are preferred, include amorphous silica compounds which function as thickening agents include, colloidal silicas compounds available under tradenames such as Cab-o-sil fumed silica manufactured by Cabot Corporation and distributed by Lenape Chemical, Bound Brook, N.J., Zeodent 165 from J. M. Huber Chemicals Division, Havre de Grace, M.d 21078, and Sylox 15 from Grace Davidson, Baltimore, Md. 21203 and precipitated silica available under the tradename Tixosil 43 from Rhone-Poulenc, Cranbury, N.J.

When the oral composition is a mouthwash, the oral vehicle includes at least one of a surface-active agent, such as sodium lauryl sulfate, a flavoring oil and also a non-toxic alcohol which also assists in dissolving the antibacterial agent.

In the aspect of the present invention wherein the oral composition is a mouthwash or liquid dentifrice, substantially liquid in character, and the vehicle particularly in a mouthwash is typically a water-alcohol mixture. Generally, the weight ratio of water to alcohol is in the range of from about 1:1 to about 20:1, preferably about 3:1 to 10:1 and more preferably about 4:1 to about 6:1. The total amount of water-alcohol mixture in this type of preparation is typically in the range of from about 70 to about 99.9% by weight. The alcohol is a non-toxic alcohol such as ethanol or isopropanol. Humectant such as glycerine and sorbitol may be present in amount of about 10–30% by weight. Liquid dentifrices typically contain about 50–85% of water, may contain about 0.5–20% by weight of non-toxic alcohol and may also contain about 10–40% by weight of humectant such as glycerine and/or sorbitol. Reference herein to sorbitol refers to the material typically as available commercially in 70% aqueous solutions. Ethanol is the preferred non-toxic alcohol. The alcohol is believed to assist in dissolving the water-insoluble non-cationic antibacterial agent as, it is believed, also does flavoring oil.

In a dental gel, water is typically present in the vehicle in amount of about 30–80% and humectant in amount of about 20–65%, each by weight of the composition.

The pH of oral compositions of the invention is generally in the range of about 4.5 to about 9 or 10 and preferably about 6.5 to about 7.5 or 8. It is noteworthy that the compositions of the invention may be applied orally at a pH below 5 without substantially decalcifying or otherwise damaging dental enamel. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc.).

The oral composition has anticaries effectiveness even without a fluoride ion source. However, it may also contain an anticaries amount of a fluoride ion source sufficient to supply about 25 ppm to 5,000 ppm of fluoride ions to improve anticaries effectiveness, particularly with respect to reducing smooth surface caries, preferably from 250 ppm to 1,500 ppm.

The sources of fluoride ions, or fluorine-providing component are well known in the art as anti-caries agents. These compounds, when present, may be slightly soluble in water or may be fully water-soluble. They are characterized by their ability to release fluoride ions in water and by substantial freedom from undesired reaction with other compounds of the oral preparation. Among these materials are inorganic fluoride salts, such as soluble alkali metal, alkaline earth metal salts, or example sodium fluoride, potassium fluoride, ammonium fluoride, a copper fluoride such as cuprous fluoride, zinc fluoride, sodium flourosilicate, ammonium fluorosilicate, sodium fluorozirconate, sodium fluorozirconate, sodium monofluorophosphate, aluminum mono-and di-fluorophosphate and fluorinated sodium calcium pyrophosphate. Alkali metal and tin fluorides, such as sodium and stannous fluorides, sodium monofluorophosphate (MFP) and mixtures thereof, are preferred.

In the present invention the antibacterial effectiveness of the noncationic antibacterial agent is surprisingly, substantially enhanced in the presence of xylitol and SLS, as demonstrated below.

When present, the antibacterial-enhancing agent (AEA) which can further enhance delivery of the noncationic antibacterial agent to, and retention thereof on, oral surfaces, is employed in amounts effective to achieve such enhancement within the range in the oral composition of about 0.05% to about 4%, preferably about 0.1% to about 3%, more preferably about 0.5% to about 2.5% by weight.

The AEA may be a simple compound, preferably a polymerizable monomer, more preferably a polymer, which latter term is entirely generic, including for example oligomers, homopolymers, copolymers of two or more monomers, and the like. The AEA may be natural or synthetic, and water insoluble or preferably water (saliva) soluble or swellable (hydratable, hydrogel forming). It has an (weight) average molecular weight of about 100 to about 1,000,000, or more, preferably about 1,000 to about 1,000,000, more preferably about 2,000 or 2,500 to about 250,000 or 500,000. The description of AEA's in ancestor U.S. Pat. Nos. 5,032,386 and 5,192,530 is incorporated herein by reference.

The AEA contains at least one delivery-enhancing group, and at least one organic retention-enhancing group.

As employed herein, the delivery-enhancing group refers to one which attaches or substantively, adhesively, cohesively or otherwise bonds the AEA (carrying the antibacterial agent) to oral (e.g. tooth and gum) surfaces, thereby "delivering" the antibacterial agent to such surfaces. The organic retention-enhancing group, generally hydrophobic, attaches or otherwise bonds the antibacterial agent to the AEA, thereby promoting retention of the antibacterial agent to the AEA and indirectly on the oral surfaces.

Preferably, the AEA is an anionic polymer and especially a polycarboxylate of molecular weight or about 1,000 to about 1,000,000 or more comprising a chain or backbone containing repeating units each preferably containing at least one carbon atom and preferably at least one directly or indirectly pendent, monovalent delivery-enhancing group and at least one directly or indirectly pendant monovalent retention-enhancing group geminally, vicinally or less preferably otherwise bonded to atoms, preferably carbon, in the chain. Preferred polycarboxylates are often employed in the form of their free acids or preferably partially or more preferably fully neutralized water soluble or water-swellable (hydratable, gel-forming) alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether, having a molecular weight (M.W.) of about 30,000 to about 1,000,000, most preferably about 30,000 to about 500,000. These copolymers are available for example as Gantrez, e.g. AM 139 (M.W. 5,000,000); AM 119 (M.W. 250,000); and preferably S-97 pharmaceutical grade (M.W. 700,000), of GAF Corporation, New York, N.Y.

An essential ingredient in the present invention is as a surface active agent, sodium lauryl sulfate. Such an organic surface-active agent is used in the oral compositions of the present invention to achieve increased prophylactic action and to impart detersive and foaming properties. Moreover, such a surface active agent assists in achieving thorough and complete dispersion of the noncationic antibacterial agent throughout the oral cavity, and render the instant compositions more cosmetically acceptable.

The sodium lauryl sulfate surface active agent is present in an amount of about 0.5 to 5% by weight, preferably about 1 to 2.5%. As indicated, the surface active agent is believed to assist in the dissolving of the noncationic antibacterial agents.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material in addition to xylitol may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents for mixture with xylitol include sucrose, lactose, maltose, sorbitol, sodium cyclamate, perillartine, APM (aspartyl phenyl alanine methyl ester), saccharine and the like, with (sodium) saccharine being preferred. Suitably, flavor and sweetening agents (excluding xylitol, which is separately present) each or together comprise from about 0.1% to 5% more of the preparation. Moreover, flavor oil is believed to aid the dissolving of the antibacterial agent together with or even in the absence of surface-active agent.

Additional materials which substantially dissolve the antibacterial agent, to permit its delivery to the soft tissues at or near the gumline, may be employed in the present invention. Typical solubilizing materials include the humectant polyols such as propylene glycol, dipropylene glycol and hexylene glycol, cellosolves such as methyl cellosolve and ethyl cellosolve, vegetable oils and waxes containing at least about twelve carbon atoms in a straight chain such as olive oil, castor oil, and petrolatum and esters such as amyl acetate, ethyl acetate, glyceryl tristearate and benzyl benzoate. Propylene glycol is preferred. As used herein, "propylene glycol" includes 1,2-propylene glycol and 1,3-propylene glycol.

When the amount of substantially water-insoluble noncationic antibacterial agent is low, say up to about 0.3% by weight, as little as about 0.5% by weight of the foregoing solubilizing agent can be sufficient to solubilize the antibacterial agent. When higher amounts such as at least about 0.5% by weight, of antibacterial agent are present, it is desirable that at least about 5% by weight, typically up to about 20% or more by weight, of the solubilizing agent be present. These amounts may be considered to be a part of the liquid vehicle of the dentifrice and in fact the solubilizing agents include polyol humectants such as propylene glycol and dipropylene glycol.

The preparation of dentifrices is well known in the art. U.S. Pat. Nos. 3,996,863, 3,980,767, 4,328,205, and 4,358,437, which are incorporated herein by reference, describe toothpastes and methods of production thereof, which may be utilized for production of the dentifrices according to the present invention. Further, discussion of the preparation of oral compositions is presented in Harry's Cosmeticology, Seventh Edition, 1982, edited by J. B. Wilkinson and R. J. Moore, published by Chemical Publishing of New York, pages 609 to 617.

More specifically, to prepare a dentifrice of the present invention, generally the humectants e.g. glycerin, propylene glycol, polyethylene glycol ingredients, are dispersed with the xylitol and any other sweetener and water in a conventional mixer, until the mixture becomes a homogeneous gel phase. Into the gel phase are added a pigment such as $TiO_2$, any acid or base required to adjust the pH, and any fluoride anticaries agents, such as sodium fluoride. These ingredients are mixed until a homogenous phase is obtained, whereupon the polishing agent/abrasive is mixed into the gel phase, prior to adding the AEA, such as Gantrex S-97. The mixture is then transferred to a high speed/vacuum mixer; wherein, the thickener, such as gum, Sylodent 15 or sodium carboxymethyl cellulose; flavor; and surfactant ingredients are added and the ingredients mixed at high speed under vacuum of from about 20 to 100 mm of Hg. The resultant product is in each case a homogeneous, semi-solid, extrudable paste product.

In the preferred practice of this invention an oral composition containing the composition of the present invention is preferably applied regularly to dental enamel, such as every day or every second or third day or preferably from 1 to 3 times daily, at a pH of about 4.5 to about 9 or 10, generally about 5.5 to about 8, preferably about 6.5 to 7.5 or 8, for at least two weeks up to eight weeks or more up to lifetime.

It will be understood that, as is conventional, the oral preparations are to be sold or otherwise distributed in suitable labeled packages. Thus a toothpaste or dental cream or gel dentifrice as well as a dental gel will usually be in a collapsible tube typically aluminum, lined lead or plastic, or other squeeze, pump or pressurized dispenser for metering out the contents, having a label describing it, in substance, as a toothpaste, dental cream or the like. A mouth rinse will generally be in a glass or plastic bottle.

The following examples are further illustrative of the nature of the present invention, but it is understood that the invention is not limited thereto. All amounts and proportions referred to herein and in the appended claims are by weight, unless otherwise indicated.

EXAMPLE 1

The following opacified dentifrice is prepared:

Formulation A

|  | Parts By Weight |
|---|---|
| Triclosan | 0.30 |
| Xylitol | 10.00 |
| Silica Polishing Agent (Zeodent 113) | 20.00 |
| Glycerin | 15.00 |
| Gantrez S97 (13.37%) | 15.00 |
| Sorbitol (70%) | 14.50 |
| Silica Thickener (Sylox 15) | 2.00 |
| Sodium Lauryl Sulfate | 1.50 |
| Sodium Hydroxide (50%) | 1.20 |
| Flavor | 1.00 |
| Sodium Carboxymethylcellulose | 0.80 |
| Propylene Glycol | 0.50 |
| Titanium Dioxide | 0.50 |
| Iota Carrageenan | 0.30 |
| Sodium Saccharin | 0.30 |
| Water | 17.10 |
| Total | 100.00 |

An experiment conducted on rats is described as follows:

Brief Summary of the Protocol

The rats are weaned (Day 20 after birth) and randomly distributed among two treatment groups of ten each. They are maintained on a cariogenic diet 2000 (56% sucrose, 28% skimmed milk powder, 8% wheat flour, 5% dried yeast, 2% Gerval Protein (Lederle Co.), and 1% NaCl) and de-ionized water ad libitum. On days 21 and 22, the rats are inoculated intra-orally, with a suspension of *Streptococcus mutans* OMZ176 and *Actinomyces viscous* Ny-1. Test dentifrices or solutions (0.1 mL) are applied twice daily by means of disposable syringes for the duration of the study. The extent of smooth-surface and fissure caries is assessed according to previously described methods (Schmid et al., 1984).

TABLE I

Results of Experimental Dentifrices on Dental Caries in Rats

| | Mean Caries Incidence per Rat (N = 10) | |
|---|---|---|
| Treatment | Dentinal Fissures | Smooth Surfaces |
| Control, $H_2O$ | 9.7 ± 1.83 | 14.8 ± 1.93 |
| Example 1 Dentifrice | 6.7 ± 4.32* | 15.0 ± 5.96 |

*Significantly different from control, P < 0.05

The results of this study indicate that the experimental dentifrice is effective in reducing caries incidences in dentinal fissures of rats.

In addition, by including a fluoride providing agent such as 0.243 parts sodium fluoride or 0.76 parts of sodium monofluorophosphate in place of corresponding amount of water, smooth surface caries are also reduced.

EXAMPLE 2

The *s. mutan* inhibition effectiveness of a formulation of the present invention, Formulation B (a commercial product having Formulation C, as presented below, to which 10% by weight Xylitol was added), was assessed in a 6 month (24 week), double-blind, clinical study with 155 participants. On a random basis about ⅓ of the participants used Formulation B twice daily, after breakfast and immediately before going to bed, abstaining from using any other dentifrice throughout the 6 month study period. Each participant was given a white, coded tube, the code not broken until all data had been analyzed. Each participant brushed by (i) using about 1.5 cm of dentifrice on a wet toothbrush, (ii) spread the toothpaste evenly in the lower and upper arch, (iii) brushed for about 2 minutes, (iv) took a sip of water together with the dentifrice and filtered the slurry between the teeth by active cheek movements for 30 seconds before expectorating, (v) avoided further rinsing with water, and (vi) avoided eating/drinking for two hours thereafter. Microbiological assessments of *S. Mutans* growth was made on samples of each participants saliva and plaque: 1) prior to the study to establish a baseline, 2) after 8 weeks, 3) after 16 weeks and 4) after 24 weeks.

Formulation C

|  | Parts By Weight |
|---|---|
| Triclosan | 0.30 |
| Silica Polishing Agent (Tixosil 103) | 20.00 |
| Glycerin | 20.00 |
| Gantrez S97 (13.37%) | 15.00 |
| Sorbitol (70%) | 19.50 |
| Silica Thickener (Tixosil 43) | 1.00 |
| Sodium Lauryl Sulfate | 1.58 |
| Sodium Hydroxide (25%) | 2.40 |
| Flavor | 1.00 |
| Cellulose Gum | 0.80 |
| Titanium Dioxide | 1.00 |
| Iota Carrageenan | 0.30 |
| Sodium Saccharin | 0.30 |
| Sodium Fluoride | 0.32 |
| Water | 16.50 |
| Total | 100.00 |

The microbiological *S. Mutans* assessments were made by collecting from each participant a sample of paraffin-stimulated whole saliva (about 3 ml), from which about 1 ml was transferred to a vial with 5.7 ml transport fluid (Syed and Loesche, "Survival Of Human Dental Plaque Flora In Various Transport Media", Applied Microbiology 24:638, 1972). Triangular sterile, wooden toothpicks were inserted into each of four approximal spaces ($^{15}/_{16}$, $^{25}/_{26}$, $^{35}/_{36}$ and $^{45}/_{46}$), the four tips with adherent plaque were cut-off and dropped into the same well in a microtiter plate containing 0.3 ml RTF. Within 24 hours the saliva samples were processed by homogenizing for 60 seconds on a Whirlimixer and the plaque samples ultrasonically treated for 10 seconds. After serial dilution in 0.05 M phosphate buffer (pH 7.3) with 0.4% KCl, 25 μl portions were spread on mitis salivarius agar, supplemented with 20% sucrose and 200 U/l bacitracin, MSB agar (see Gold et al., "A Selective Medium for the Isolation of *Streptococcus Mutans*", Archieves of Oral Biology 18:1357, 1973). The plates were incubated in jars filled with 95% $N_2$ and 5% $CO_2$ for 48 hours at 37° C. The identification of *S. Mutans* was based on colony morphology as described by Emilson (see C. G. Emilson, "Prevalence Of *Streptococcus Mutans* With Different Colonial Morphologies In Human Plaque And Siliva", Scandinavian Journal of Dental Research 12:26, 1983). Doubtful colonies were isolated and checked by iminunofluorescence using specific antibodies (D. Bratthall, "Immunoflourescent Identification of *Streptococcus mutans*", Odontologisk Revy 23:1, 1972). For analysis the number of *S. Mutans* were transformed to a logrithmic basis and as log of colony-forming units (CFU) per millilitre saliva and as log of CFU per plaque sample. The mean decrease (log CFU/ml) of Formulation B in the participants saliva at 8, 16 and 24 weeks is presented in Table II, below. The mean decrease (log CFU/ml) of Formulation B in the participants plaque at 8, 16, and 24 weeks is presented in Table III, below.

For comparative purposes, the 6 month (24 week) procedure of Example 2 was repeated with groups of 51–52 participants using the commercial Formulation C, and Formulation D, the same formulation as Formulation C, except triclosan, and Gantrez S97 were removed and additional water added in their place. The mean decrease (log CFU/ml) of comparative Formulations C and D, with respect to *S. Mutans*, within the participants saliva and plaque are presented in Tables II and III, respectively.

TABLE II

Reduction of S. Mutans in Saliva of Participants

|  | 8 Week log CFU/ml mean decrease (+/− Std. Deviation) | 16 Weeks log CFU/ml mean decrease (+/− Std. Deviation) | 24 Weeks log CFU/ml mean decrease (+/− Std. Deviation) |
|---|---|---|---|
| Formulation B | 0.325 (+/− .336) | 0.575 (+/− .402) | 0.806 (+/− .438) |
| Formulation C | 0.189 (+/− .624) | 0.166 (+/− .526) | 0.258 (+/− .947) |
| Formulation D | 0.047 (+/− .606) | 0.046 (+/− .561) | 0.197 (+/− .756) |

TABLE III

Reduction of S. Mutans in Plaque of Participants

|  | 8 Week log CFU/ml mean decrease (+/− Std. Deviation) | 16 Weeks log CFU/ml mean decrease (+/− Std. Deviation) | 24 Weeks log CFU/ml mean decrease (+/− Std. Deviation) |
|---|---|---|---|
| Formulation B | 0.394 (+/− .529) | 0.603 (+/− .576) | 0.892 (+/− .803) |
| Formulation C | 0.103 (+/− .882) | 0.290 (+/− 1.171) | −.106 (+/− 1.141) |
| Formulation D | 0.186 (+/− .940) | 0.182 (+/− .842) | −.126 (+/− 1.059) |

Referring to Tables II and III, Formulation B of the present invention demonstrated consistent and significant reduction in *S. Mutans*, at $p<0.01$ and $p<0.001$, respectively by paired t-tests. Further, the longer Formulation B was used the more pronounced the reduction in *S. Mutans* observed. By analysis of variance, in relation to comparative Formulations C and D, Formulation B showed significantly greater reduction in saliva *S. Mutans* at 16 and 24 weeks ($p<0.01$) and significantly greater reduction in plaque *S. Mutans* at 24 weeks ($p<0.001$).

EXAMPLE 3

The following translucent dentifrice is prepared:

| | Parts By Weight |
|---|---|
| Triclosan | 0.30 |
| Xylitol | 10.00 |
| Silica Polishing Agent (Zeodent 113) | 20.00 |

-continued

| | Parts By Weight |
|---|---|
| Glycerin | 15.00 |
| Gantrez S97 (13.37%) | 15.00 |
| Sorbitol (70%) | 14.50 |
| Silica Thickener (Sylox 15) | 2.00 |
| Sodium Lauryl Sulfate | 1.50 |
| Sodium Hydroxide (50%) | 1.20 |
| Flavor | 1.00 |
| Sodium Carboxymethylcellulose | 0.80 |
| Titanium Dioxide | 0.50 |
| Iota Carrageenan | 0.30 |
| Sodium Saccharin | 0.30 |
| Water | 17.60 |

EXAMPLE 4

The following opacified dentifrice is prepared:

| | Parts By Weight |
|---|---|
| Triclosan | 0.30 |
| Xylitol | 10.00 |
| Silica Polishing Agent (Zeodent 113) | 20.00 |
| Glycerin | 15.00 |
| Sorbitol (70%) | 14.50 |
| Silica Thickener (Sylox 15) | 2.00 |
| Sodium Lauryl Sulfate | 1.50 |
| Sodium Hydroxide (50%) | 1.20 |
| Flavor | 1.00 |
| Sodium Carboxymethylcellulose | 0.80 |
| Propylene Glycol | 0.50 |
| Titanium Dioxide | 0.50 |
| Iota Carrageenan | 0.30 |
| Sodium Saccharin | 0.30 |
| Water | 32.10 |

EXAMPLE 5

The following mouthrinse is prepared:

| | Parts by Weight |
|---|---|
| Triclosan | 0.03 |
| Xylitol | 1.0 |
| Ethanol | 10.0 |
| Propylene Glycol | 7.0 |
| Sorbitol | 10.0 |
| Glycerol | 10.0 |
| Sodium Lauryl Sulfate | 0.25 |
| Tauranol | 0.20 |
| Flavor | 0.10 |
| Water Q.S. to | 100.00 |

EXAMPLE 6

The following dental gel is prepared:

| | Parts by Weight |
|---|---|
| Triclosan | 0.3 |
| Xylitol | 10.0 |
| Sodium Lauryl Sulfate | 0.6 |
| Flavor | 1.0 |
| Iota Carragunan | 0.65 |

-continued

|  | Parts by Weight |
| --- | --- |
| NaCMC | 2.0 |
| Glycerine | 20.0 |
| Propylene Glycol | 0.5 |
| Silica Thickener (Sylox 15) | 5.0 |
| Sorbitol | 15.0 |
| Tauranol | 0.25 |
| Sodium Saccharine | 0.1 |
| Sodium Fluoride | 0.243 |
| Water Q.S. to | 100.00 |

This invention has been described with respect to certain preferred embodiments and it will be understood that modifications and variations thereof obvious to those skilled in the art are to be included within the purview of this application and the scope of the appended claims.

We claim:

1. A process of reducing caries formation comprising preparing an antibacterial oral composition which is free of a fluoride ion releasing compound and contains an effective antiplaque amount of a substantially water insoluble noncationic antimicrobial agent, at least about 0.1% by weight of xylitol, and at least 0.5% sodium lauryl sulfate, and an antibacterial-enhancing agent, applying the antibacterial oral composition to the oral surfaces and thereby inhibiting the growth of *streptococcus mutans*.

2. The process claimed in claim 1 wherein said antibacterial agent is present in amount of about 0.01–5% by weight.

3. The process claimed in claim 2 wherein said antibacterial agent is triclosan.

4. The process claimed in claim 3 wherein said amount of said antibacterial agent is about 0.3–0.5% by weight.

5. The process claimed in claim 1 wherein xylitol is present in amount of about 0.1–5% by weight.

6. The process claimed in claim 1 wherein xylitol is present in amount of about 3–25% by weight.

7. The process claimed in claim 6 wherein xylitol is present in amount of about 5–20% by weight.

8. The process claimed in claim 1 wherein xylitol is present in amount of about 20–40% by weight.

9. The process claimed in claim 1 wherein said antibacterial-enhancing agent is a polycarboxylate.

10. The process claimed in claim 1 wherein said process additionally comprises about 0.1–5% by weight of a flavoring oil.

11. The process claimed in claim 1, wherein said antibacterial agent is selected from the group consisting of halogenated diphenyl ethers, benzoic acids, halogenated carbanilides and phenolic compounds.

12. The process claimed in claim 11, wherein said antibacterial agent is a halogenated diphenyl ether.

13. The process of claim 9 wherein the polycarboxylate is a maleic anhydride/methyl vinyl ether copolymer.

14. The process of claim 1 wherein the oral composition is a mouth rinse.

15. The process of claim 1 wherein the oral composition is a dental paste.

16. The process of claim 1 wherein the oral composition is a dental gel.

* * * * *

UNITED STATES PATENT AND TRADEMARK OFFICE
CERTIFICATE OF CORRECTION

| | |
|---|---|
| PATENT NO. | : 6,136,298 |
| DATED | : January 20, 1999 |
| INVENTOR(S) | : Gaffar et al. |

Page 1 of 1

It is certified that error appears in the above-identified patent and that said Letters Patent is hereby corrected as shown below:

Title page, column 1,
Item [63] should read -- Continuation-in-part of application No. 08/968,671, Nov. 12, 1997, abandoned; 08/775,059, Dec. 27, 1996, abandoned; 08/466,651, June 6, 1994.

Signed and Sealed this

Twenty-fifth Day of September, 2001

Attest:

NICHOLAS P. GODICI
*Attesting Officer*   *Acting Director of the United States Patent and Trademark Office*

UNITED STATES PATENT AND TRADEMARK OFFICE
CERTIFICATE OF CORRECTION

PATENT NO.   : 6,136,298
DATED        : October 24, 2000
INVENTOR(S)  : Gaffar et al.

It is certified that error appears in the above-identified patent and that said Letters Patent is hereby corrected as shown below:

<u>Title page,</u>
Item [63], should read -- Continuation-in-part of application No. 08/968.671, Nov. 12, 1997, abandoned; 08/775,059, Dec. 27, 1996, abandoned; continuation of application No. 08/466,651, June 6, 1995, abandoned; divisional of application No. 08/275,469, July 14, 1994, granted U.S. Patent No. 5,531,982. --

Signed and Sealed this

Twenty-third Day of July, 2002

*Attest:*

*Attesting Officer*

JAMES E. ROGAN
*Director of the United States Patent and Trademark Office*